US007737188B2

(12) United States Patent
McGown et al.

(10) Patent No.: US 7,737,188 B2
(45) Date of Patent: Jun. 15, 2010

(54) REVERSIBLE BIOGEL FOR MANIPULATION AND SEPARATION OF SINGLE-WALLED CARBON NANOTUBES

(75) Inventors: Linda McGown, Troy, NY (US); Omkaram Nalamasu, San Jose, CA (US); Yuehua Yu, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 12/234,257

(22) Filed: Sep. 19, 2008

(65) Prior Publication Data

US 2009/0111897 A1 Apr. 30, 2009

Related U.S. Application Data

(63) Continuation of application No. PCT/US2007/004866, filed on Feb. 23, 2007.

(60) Provisional application No. 60/785,493, filed on Mar. 24, 2006.

(51) Int. Cl.
*B01J 13/00* (2006.01)
(52) U.S. Cl. ...................................... 516/106
(58) Field of Classification Search .................. 516/102
See application file for complete search history.

(56) References Cited

U.S. PATENT DOCUMENTS

| 2003/0168385 A1 | 9/2003 | Papadimitrakopoulos |
| 2004/0241718 A1 | 12/2004 | McGown |
| 2005/0009039 A1 | 1/2005 | Jagota et al. |
| 2006/0054555 A1 | 3/2006 | Sun |

FOREIGN PATENT DOCUMENTS

| WO | WO 2006/100647 A1 | 9/2006 |
| WO | WO 2008/048352 A2 | 4/2008 |

OTHER PUBLICATIONS

A Reversible Gel for Chiral Separations, Dowling et al., Analytical Chemistry, vol. 76, No. 15, Aug. 1, 2004, p. 4558-4563.*
Andrisano et al., Enantioselective extraction of dinitrophenyl amino acids mediated by lipophilic deoxyguanosine derivatives: chiral discrimination by self-assembly. Angew Chem Int Ed Engl. Aug. 1999;38(16):2386-2388.
Bianco et al., Applications of carbon nanotubes in drug delivery. Curr Opin Chem Biol. Dec. 2005;9(6):674-9. Epub Oct. 17, 2005. Review.
Case et al., Guanosine gel for sequence-dependent separation of polymorphic ssDNA. Electrophoresis. Aug. 2007;28(17):3008-16.
Chantot et al., Physico-chemical properties of nucleosides. 4. Gel formation by quanosine and its analogues. Biochimie. 1971;53(3):347-54.
Chantot et al., Nucleoside conformations. XIII. Circular dichroïsm of guanosine gels and the conformation of GpG and poly (G). Biochimie. 1974;56(4):501-7.
Chattopadhyay et al., A route for bulk separation of semiconducting from metallic single-wall carbon nanotubes. J Am Chem Soc. 2003;125(11):3370-5.
Chen et al., Dissolution of full-length single-walled carbon nanotubes. J Phys Chem B. 2001;105(13):2525-8.
Chen et al., Solution properties of single-walled carbon nanotubes. Science. Oct. 2, 1998;282(5386):95-8.
Cromwell et al., Protein aggregation and bioprocessing. AAPS J. Sep. 15, 2006;8(3):E572-9.
Davis, G-quartets 40 years later: from 5'-GMP to molecular biology and supramolecular chemistry. Angew Chem Int Ed Engl. Jan. 30, 2004;43(6):668-98.
Dowling et al., A guanosine biogel: chiral separations in capillary electrophoresis and spectroscopic studies.. Student Exams Seminar dated Friday May 27, 2005. Event information page online at http://www.chem.duke.edu/calendar/view.php?user=chem&abstract-695. Accessed online Jun. 12, 2006.
Dresselhaus et al., Raman spectroscopy on isolated single wall carbon nanotubes. Carbon. 2002;40(12):2043-61.
Gellert et al., Helix formation by guanylic acid. Proc Natl Acad Sci U S A. Dec. 15, 1962;48:2013-8.
Grainger, Controlled-release and local delivery of therapeutic antibodies. Expert Opin Biol Ther. Jul. 2004:4(7):1029-44. Review.
Guschlbauer et al., Four-stranded nucleic acid structures 25 years later: from guanosine gels to Telomer DNA. J Biomol Struct Dyn. Dec. 1990;8(3):491-511. Review.
Holzinger et al., Sidewall functionalization of carbon nanotubes. Angew Chem Int Ed Engl. Nov. 5, 2001;40(21):4002-4005.
Ikeda et al., Water-solubilization of nucleotides-coated single-walled carbon nanotubes using a high-speed vibration milling technique. Org Lett. Mar. 16, 2006;8(6):1153-6.
Islam et al., High weight fraction surfactant solubilization of single-wall carbon nanotubes in water. Nano Lett. 2003;3(2):269-73.
Krupke et al., Separation of metallic from semiconducting single-walled carbon nanotubes. Science. Jul. 18, 2003;301(5631):344-7. Epub Jun. 26, 2003.
Li et al., Carbon nanotubes as support for cathode catalyst of a direct methanol fuel cell. Carbon. Apr. 2002;40(5):791-4.
Liu et al., Fullerene pipes. Science. May 22, 1998;280(5367):1253-6.
Liu, Modifications of carbon nanotubes with polymers. Eur Polymer J. Nov. 2005;41(11):2693-2703.

(Continued)

*Primary Examiner*—Ling-Siu Choi
*Assistant Examiner*—Chun-Cheng Wang
(74) *Attorney, Agent, or Firm*—Wolf, Greenfield & Sacks, P.C.

(57) ABSTRACT

The invention provides the use of novel, binary guanosine gels for simple, rapid and nondestructive solubilization of individual single walled carbon nanotubes (SWNTs) at high concentrations. The gels exhibit selectivity between metallic and semiconducting SWNTs and, further, among SWNTs with different chiralities.

14 Claims, No Drawings

OTHER PUBLICATIONS

Maeda et al., Large-scale separation of metallic and semiconducting single-walled carbon nanotubes. J Am Chem Soc. Jul. 27, 2005;127(29):10287-90.

McGown, A novel gel phase for capillary electrophoresis. Nov. 2005 CSSC Meeting Abstract. Nov. 1, 2005. The University of Connecticut. Storrs, CT.

Mickelson et al., Solvation of fluorinated single-wall carbon nanotubes in alcohol solvents. J Phys Chem B. 1999;103(21):4318-22.

O'Connell et al., Band gap fluorescence from individual single-walled carbon nanotubes. Science. Jul. 26, 2002;297(5581):593-6.

O'Connell et al., Reversible water-solubilization of single-walled carbon nanotubes by polymer wrapping. Chem Phys Lett. Jul. 13, 2001;342(3-4):265-71.

Ortiz-Acevedo et al., Diameter-selective solubilization of single-walled carbon nanotubes by reversible cyclic peptides. J Am Chem Soc. Jul. 6, 2005;127(26):9512-7.

Pantarotto et al., Functionalized carbon nanotubes for plasmid DNA gene delivery. Angew Chem Int Ed Engl. Oct. 4, 2004;43(39):5242-6.

Prato et al., Functionalized carbon nanotubes in drug design and discovery. Acc Chem Res. Jan. 2008;41(1):60-8. Epub Sep. 15, 2007. Review.

Proni et al., The chirality of the cholesteric phases of DNA and G-wires: its connection to their molecular structures. Chemistry. Sep. 1, 2000;6(17):3249-53.

Rao et al., Effect of van der Waals interactions on the Raman modes in single walled carbon nanotubes. Phys Rev Lett. Apr. 23, 2001;86(17):3895-8.

Sasisekharan et al., The structure of helical 5'-guanosine monophosphate. J Mol Biol. Feb. 25, 1975;92(2):171-9.

Simonsson, G-quadruplex DNA structures—variations on a theme. Biol Chem. Apr. 2001;382(4):621-8. Review.

Sreenivasachary et al., Structural selection in G-quartet-based hydrogels and controlled release of bioactive molecules. Chem Asian J. Jan. 4, 2008;3(1):134-9.

Sreenivasachary et al., Gelation-driven component selection in the generation of constitutional dynamic hydrogels based on guanine-quartet formation. Proc Natl Acad Sci U S A. Apr. 26, 2005;102(17):5938-43. Epub Apr. 19, 2005.

Tulis et al., YC-1-mediated vascular protection through inhibition of smooth muscle cell proliferation and platelet function. Biochem Biophys Res Commun. Mar. 8, 2002;291(4):1014-21.

Walmsley et al., A new model for the K+-induced macromolecular structure of guanosine 5'-monophosphate in solution. Biochemistry. Oct. 19, 1999;38(42):14063-8.

Wang et al., Rapidly functionalized, water-dispersed carbon nanotubes at high concentration. J Am Chem Soc. Jan. 11, 2006;128(1):95-9.

Wei et al., Microfabrication technology: organized assembly of carbon nanotubes. Nature. Apr. 4, 2002;416(6880):495-6.

Wohlstadter et al., Carbon nanotube-based biosensor. Adv Materials. Jul. 2003;15(14):1184-7.

Yakobson et al., Fullerene nanotubes: $C_{1,000,000}$ and beyond. American Scientist. Jul.-Aug. 1997;324:337. Accessed online at http://www.americanscientist.org/issues/num2/fullerene-nanotubes-c1000000-and-beyond/1.

Yu et al., Capillary electrophoresis: detection and applications. Guanosine gels as a mobile phase for chiral separation of single-walled carbon nanotubes in capillary electrophoresis. Mar. 15, 2006. Meeting Abstract #1410-8.

Yu et al., Tunable thermoassociation of binary guanosine gels. J Phys Chem B. Jan. 31, 2008;112(4):1130-4. Epub Jan. 9, 2008.

Zhao et al., Synthesis and characterization of water soluble single-walled carbon nanotube graft copolymers. J Am Chem Soc. Jun. 8, 2005;127(22):8197-203.

Zheng et al., DNA-assisted dispersion and separation of carbon nanotubes. Nat Mater. May 2003;2(5):338-42.

International Search Report and Written Opinion dated Apr. 23, 2008 in connection with Application No. PCT/US07/04866.

International Preliminary Report on Patentability dated Apr. 7, 2009 in connection with Application No. PCT/US07/04866.

Chen et al., Bulk separative enrichment in metallic or semiconducting single-walled carbon nanotubes. Nanoletters. Aug. 20, 2003;3(9):1254-9.

Davis et al., Supramolecular architectures generated by self-assembly of guanosine derivatives. Chem Soc Rev. Feb. 2007;36(2):296-313. Epub Nov. 7, 2006.

Extended European Search Report mailed Nov. 24, 2009 in connection with corresponding EP Application No. 07861249.6.

\* cited by examiner

REVERSIBLE BIOGEL FOR MANIPULATION AND SEPARATION OF SINGLE-WALLED CARBON NANOTUBES

RELATED APPLICATION

This application is a continuation of PCT/US2007/004866 filed on Feb. 23, 2007, and claims the benefit of U.S. Provisional Application No. 60/785,493, filed on Mar. 24, 2006. The entire teachings of the above application are incorporated herein by reference.

BACKGROUND OF THE INVENTION

Carbon exists in at least 8 different allotypes, one of which is a nanotube form.

The unique properties of carbon nanotubes (CNTs), more specifically, single walled carbon nanotubes (SWNT) have made them excellent candidates for applications in bio-sensing, (Wohlstadter, J. N., et al., Adv. Mat. 2003, 15, 1184), gene delivery (Pantarotto, D., et al., Angew. Chem., Int. Ed. 2004, 43, 5242), fuel cells (Li, W., et al., Carbon 2002, 40, 791) and nanofabrication (Wei, B. O., et al., Nature 2002, 416, 495).

Single walled carbon nanotubes (SWNTs) are hollow, tubular fullerene molecules consisting essentially of sp2-hybridized carbon atoms typically arranged in hexagons and pentagons. SWNTs typically have diameters in the range of about 0.5 nanometers (nm) and about 3.5 nm, and lengths usually greater than about 50 nm (B. I. Yakobson and R. E. Smalley, American Scientist, 1997, 324 337; Dresselhaus, et al., Science of Fullerenes and Carbon Nanotubes, 1996, San Diego: Academic Press, Ch. 19). SWNTs are distinguished from each other by a double index (n, m), where n and m are integers that describe how to cut a single strip of hexagonal graphite such that its edges join seamlessly when the strip is wrapped onto the surface of a cylinder. When n=m, the resultant tube is said to be of the "armchair" or (n, n) type, since when the tube is cut perpendicularly to the tube axis, only the sides of the hexagons are exposed and their pattern around the periphery of the tube edge resembles the arm and seat of an armchair repeated n times. When m=0, the resultant tube is said to be of the "zig-zag" or (n, 0) type, since when the tube is cut perpendicular to the tube axis, the edge is a zig-zag pattern. Where n≠m and m≠0, the resulting tube has chirality and contains a helical twist to it, the extent of which is dependent upon the chiral angle.

Considerable research effort has therefore been devoted to development of methods to achieve stable suspensions of highly dispersed CNTs (Chen, J., et al., Science 1998, 282, 95; Liu, J., et al., Science 1998, 280, 1253; Wang, Y., et al., J. Am. Chem. Soc. 2006, 128, 95; Holzinger, M., et al., Angew. Chem., Int. Ed. 2001, 40, 4002; Mickelson, E. T., et al., J. Phys. Chem. B 1999, 103, 4318; Zheng, M., et al., Nature Materials 2003, 2, 338; Ortiz-Acevedo, A., et al., J. Am. Chem. Soc. 2005, 127, 9512; O'Connell, M. J., et al., Chem. Phys. Lett. 2001, 342, 265; Liu, P. European Polymer Journal 2005, 41, 2693; Zhao, B., et al., J. Am. Chem. Soc. 2005, 127, 8197; Chen, J., et al., J. Phys. Chem. B 2001, 105, 2525; O'Connell, M. J., et al., Science 2002, 297, 593 and Islam, M. F., et al., Nano Lett. 2003, 3, 269).

Progress, however, has been impeded, by two major hurdles. First, their poor solubility in both aqueous and organic solvents makes them difficult to manipulate and functionalize. Second, CNTs are generally formed as heterogeneous mixtures of metallic and semiconducting tubes with varying chiralities. In order to separate and purify the different forms of CNTs in a sample, they must first be solubilized in an appropriate medium.

Consequently, there remains a long felt need for methods to achieve simple, rapid and nondestructive solubilization of carbon nanotubes and SWNTs in particular.

SUMMARY OF THE INVENTION

The present invention provides the use of novel, binary guanosine gels for simple, rapid and nondestructive solubilization of individual single walled carbon nanotubes (SWNTs) at high concentrations. The gels exhibit selectivity between metallic and semiconducting SWNTs and among SWNTs with different chiralities.

The present invention includes binary gels and further, gels based on combinations of at least two guanosine compounds, in which a hydrophilic (highly soluble in water) guanosine compound is mixed with a relatively insoluble hydrophobic guanosine compound.

Accordingly, one embodiment of the invention provides binary guanosine gels comprising guanosine (GUO) and guanosine 5' monophosphate (GMP) wherein the ratio of GUO:GMP is from about 0.1 to about 2.

In one embodiment the ratio of GUO:GMP is 0.25.
In one embodiment the ratio of GUO:GMP is 0.2.
In one embodiment the ratio of GUO:GMP is 0.08.

The gels of the present invention are unique in that they demonstrate a range of thermoresponsive behavior including thermoassociative behavior. Accordingly, in one embodiment the gels of the present invention have a viscosity which is observably higher at room temperature than it is at a temperature less than room temperature such as on refrigeration.

The thermoassociative behavior of the binary guanosine gels of the present invention is also observably stable over a wide range of pH. Thus, in accordance with the present invention the preferred gels have a pH in the range of between about 5.0 and about 9.0.

In one embodiment of the invention, the binary guanosine gels have a potassium chloride concentration of at least 0.01 M. This concentration may, however be in the range of between about 0.01 to 0.5 M.

The binary gels of the present invention have been found to be useful in solubilizing and separating single walled carbon nanotubes (SWNTs). Unexpectedly this solubilization results in the partitioning metallic SWNT from semiconductive SWNTs. Therefore, in one embodiment of the invention is provided a method of enriching the fraction of metallic nanotubes in a sample comprising solubilizing individual single walled carbon nanotubes (SWNTs) in the binary guanosine gels of the invention.

Furthermore, the gels have shown promise in partitioning SWNTs by chirality. Therefore, in one embodiment of the invention is provided a method of partitioning single walled carbon nanotubes (SWNTs) by chirality comprising solubilizing said SWNTs in the binary guanosine gels of the invention.

DETAILED DESCRIPTION OF THE INVENTION

A description of preferred embodiments of the invention follows.

According to the present invention, disclosed herein are binary guanosine gels formed by mixing soluble guanosine-5'-monophosphate (GMP) with insoluble guanosine (Guo) that exhibit unique properties that make them highly effective for SWNT dispersion.

Guanosine gels, or "G-gels", formed by individual guanosine compounds have been extensively studied (Gellert, M., et al., Proc. Natl. Acad. Sci. 1962, 48, 2013; Sasisekharan, V., and Zimmerman, S.; Davies, D. R. J. Mol. Biol. 1975, 92, 171; Proni, G., et al., Chem. Eur. J. 2000, 6, 3249; Walmsley, J. A. and Burnett, J. F. Biochemistry 1999, 38, 14063 and Davis, J. T. Angew. Chem. Int. Ed. 2004, 43, 668).

The basic building block is the G-quartet formed by Hoogsteen hydrogen bonding between each of four guanines and its two nearest neighbors. As the monomer concentration increases, the G-quartets can aggregate into columnar stacks through $\pi$-$\pi$ interactions or, in the case of 5'-guanosine monophosphate (GMP), into continuous, hydrogen-bonded helices.

It is demonstrated herein that by combining the soluble GMP with the insoluble Guo in particular ratios in aqueous solution, the resulting solutions are shown to form reversible, binary G-gels with unique chiral and thermoresponsive properties that can be controlled by adjusting the Guo:GMP ratio, cation content and pH. The chirality of G-gels offers the possibility of chiral selectivity that is supported by previous work demonstrating separations of small molecules using G-gels (Dowling, V. A., et al., Anal. Chem. 2004, 15, 4558; McGown, US Pregrant Publication 2004/0241718, published Dec. 2, 2004).

Specifically, in some proportions the gels of the present invention are formed by self-association of guanosine and 5'-guanosine monophosphate that are solution at low temperatures and then become a firm gel at higher temperatures before melting at even higher temperatures. As used herein, low temperatures are below room temperature and are between 2-20° C. while room temperature is defined as between 20-27° C. and high temperatures are defined as those above room temperature, particularly above 35° C., above 45° C., above 55° C., above 65° C. or above 100° C.

It is noted that the actual transition temperatures will vary depending upon the specific gel recipe, but in general the solution phase exists below room temperature, the gel exits at and above room temperature, and the higher temperature melting occurs above 40-50° C.

This unique thermal dependence makes this gel ideal for encapsulation of heat sensitive components such as living cells, enzymes and other biological components, since they could be added to the solution at low temperature for homogeneous distribution and then raised to room or body temperature for gelation into, for example, drug delivery devices, artificial cells, artificial tissues, artificial organs, or bioreactors for medical use or environmental bioremediation.

Similarly, nanocomponents such as carbon nanotubes (CNTs) or CNT-biological hybrids can be dispersed and stored in the solutions at low temperatures and then immobilized in the gels for use at higher temperatures. As such, nanostructures comprised of CNTs may be incorporated into the binary gels for use in applications such as fuel cells, solar cells, artificial cells or tissues for medical purposes, microreactors containing cells or enzymes for bioremediation and/or drug delivery.

Furthermore, it is shown here that binary G-gels provide selective solubilization and dispersion of individual SWNTs, presumably through selective interactions of the nanotubes with the aromatic guanines in the chiral G-gel structures.

EXAMPLES

Example 1

Binary G-gels: Thermoassociative Observations

Solutions of guanosine (Guo) and guanosine 5'monophosphate (GMP) in buffer (25 mM Tris buffer, pH 7.2) and then refrigerated as liquids overnight were evaluated for phase changes in different temperature ranges and across a range of cation concentration. The data are shown in Table 1. It is noted that the buffer may be modified to any suitable buffer and may even comprise water alone. The buffer may also contain cations other than potassium or no cations at all. The phase observations labeled in the table include "L" for liquid, "VL" for viscous liquid and "G" for gel. The symbol "–" indicates no observation data for this temperature range.

TABLE 1

| | Binary G-gels | | | | |
| | | | | Observation | |
| gel ID | GUO/GMP [M] | KCl [M] | Low Temp (5° C.) | Room Temp. (25° C.) | High Temp. (above 40° C.) |
| --- | --- | --- | --- | --- | --- |
| 1056 | 0.00625/0.025 | 0.0125 | VL | L | — |
| 1057 | 0.0125/0.05 | 0.025 | G | VL | — |
| 1058 | 0.025/0.1 | 0.05 | L | G | — |
| 1059 | 0.05/0.2 | 0.1 | L | VL | G |

The data suggest that at a GUO:GMP ratio of 1:4, the thermoassociative properties of the gel (from liquid to gel on increased temperature; see ID 1058) occurs and is enhanced at higher concentrations of monomer. Compare ID 1058 with ID 1059.

Example 2

Binary G-Gels: Timing of Thermoassociation

Additional studies were performed with samples having monomer concentrations between those of gel ID 1058 and 1059. Samples were prepared according to the concentrations in the table (25 mM Tris buffer, pH 7.2) and then refrigerated as liquids overnight. These data are shown in Table 2. The time, in minutes, that each sample took to reach a gel state once at room temperature was also measured. These data are listed in the table in the room temperature column. The phase observations labeled in the table include "L" for liquid, "VL" for viscous liquid and "G" for gel. The symbol "–" indicates no observation data for this temperature range.

TABLE 2

| | Additional binary G-gels | | | | |
| | | | | Observation | |
| gel ID | GUO/GMP [M] | KCl [M] | Low Temp (5° C.) | Room Temp. (25° C.) | High Temp. (above 40° C.) |
| --- | --- | --- | --- | --- | --- |
| 1063 | 0.03/0.12 | 0.06 | L | G (14 min) | — |
| 1064 | 0.035/0.14 | 0.07 | L | G (23 min) | — |

TABLE 2-continued

Additional binary G-gels

| gel ID | GUO/GMP [M] | KCl [M] | Observation | | |
|---|---|---|---|---|---|
| | | | Low Temp (5° C.) | Room Temp. (25° C.) | High Temp. (above 40° C.) |
| 1065 | 0.04/0.16 | 0.08 | L | G (35 min) | — |
| 1066 | 0.045/0.18 | 0.09 | L | VL (did not gel at RT) | — |

The data shown here suggest that while maintaining a GUO/GMP ratio of 1:4, higher monomer concentrations expand the temperature window of the low temperature liquid phase.

Example 3

Binary G-gels: Effect of Cation Concentration

The effects of cation concentration were investigated. Samples containing 0.025M guanosine and 0.1M guanosine 5' monophosphate were prepared having concentrations of 0.01 M, 0.03 M, 0.05 M, 0.07 M or 0.09 M potassium chloride (KCl) (25 mM Tris buffer, pH 7.2). The phase data are shown in Table 3. The phase observations labeled in the table include "L" for liquid, "VL" for viscous liquid and "G" for gel. The symbol "–" indicates no observation data for this temperature range.

TABLE 3

Effect of cation concentration

| gel ID | GUO/GMP [M] | KCl [M] | Observation | | |
|---|---|---|---|---|---|
| | | | Low Temp (5° C.) | Room Temp. (25° C.) | High Temp. (above 40° C.) |
| 1051 | 0.025/0.1 | 0.01 | VL | G | — |
| 1052 | 0.025/0.1 | 0.03 | L | G | — |
| 1053 | 0.025/0.1 | 0.05 | L | G | — |
| 1054 | 0.025/0.1 | 0.07 | L | G | — |
| 1055 | 0.025/0.1 | 0.09 | L | G | — |

The data suggest that, while at the lowest concentration of KCl the phase transition is slightly shifted, the phase transition properties of the gel remain constant across a range of cation concentration.

Example 4

Binary G-gels: Effect of pH

Using the same binary G-gel (0.025/0.1; GUO:GMP), the effects of pH were investigated. The data are shown in Table 4. Samples were prepared (25 mM Tris buffer, pH 7.2) and then refrigerated as liquids overnight. The time, in minutes, that each sample took to reach a gel state once at room temperature was also measured. These data are listed in the table in the room temperature column. The phase observations labeled in the table include "L" for liquid, "VL" for viscous liquid and "G" for gel. The symbol "–" indicates no observation data for this temperature range.

TABLE 4

Effect of pH

| gel ID | GUO/GMP [M] | pH | Observation | | |
|---|---|---|---|---|---|
| | | | Low Temp (5° C.) | Room Temp. (25° C.) | High Temp. (above 40° C.) |
| 1072 | 0.025/0.1 | 7.2 | L | G (15 min) | — |
| 1073 | 0.025/0.1 | 8.0 | L | G (15 min) | — |
| 1074 | 0.025/0.1 | 8.8 | L | G (15 min) | — |

As shown in the table, the observed properties of the gels remained the same over the pH range of 7.2-8.8.

Example 5

Binary G-gels: Observation Matrix

An observation matrix of samples was prepared across a range of GUO and GMP concentrations. In this experiment, all samples were prepared having a GUO:GMP ratio of 1:4, pH 7.2 and KCl concentration of 0.05M in x buffer. (25 mM Tris buffer, pH 7.2).

The binary gels were observed at three temperature ranges, low temperature, room temperature and high temperature. The resultant observations are shown in Table 5 in the order of low temperature observation/room temperature observation/high temperature observation. The concentration of GUO is given in the last row running across the matrix, while the concentration of GMP is given in the first column running down the matrix. The observations are labeled in the table include "L" for liquid, "VL" for viscous liquid and "G" for gel. The symbol "–" indicates no data for this temperature.

TABLE 5

Observation matrix

| GMP [M] | Observation | | | | | |
|---|---|---|---|---|---|---|
| 0.20 | L/L/— | L/L/— | L/L/— | L/VL/— | L/VL/— | —/L/G |
| 0.15 | L/L/— | L/L/— | L/VL/— | L/VL/— | —/L/G | L/G/— |
| 0.10 | L/L/— | L/L/— | L/G/— | L/G/— | L/G/— | VL/G/— |
| 0.05 | L/L/— | VL/VL/— | G/G/— | G/G/— | G/G/— | G/G/— |
| 0.0 | L/L/— | L/L/— | L/L/— | L/L/— | L/L/— | L/L/— |
| GUO [M] | 0.0 | 0.01 | 0.02 | 0.03 | 0.04 | 0.05 |

As other data herein have suggested, the most notable gel behavior occurs at higher concentrations of both monomers where the gels become viscous liquids on increased temperature.

Additional studies have failed to identify an upper boundary for the concentration of the monomers in preparing these binary gels. This boundary might only be reached at the solubility of each monomer.

Example 6

Preparation of SWNT Suspensions

The binary G-gels disclosed herein exhibit thermoassociative behavior with gelation temperatures that decrease with increasing SWNT concentration. Single walled carbon nanotubes (SWNTs) were solubilized in G-gels formed by mixtures of guanosine and 5'-guanosine monophosphate in aqueous solution.

Three different guanosine media were investigated. In all cases, SWNT suspensions were prepared by sonicating SWNTs in the dispersing media in bath sonicator for 15 min. Stable suspensions of as much as 5 mg/mL could be achieved simply by sonicating.

As a control or reference, the first medium was 0.25 M GMP alone in 25 mM Tris buffer, pH 7.2. GMP is highly soluble in water and does not readily form higher order structures in the absence of stabilizing K+. In contrast to the binary gels described below, up to 1.4 mg/mL SWNT could be solubilized for up to 24 h in 0.25 M GMP without Guo, after which the SWNTs precipitated. The temporary suspension could be reformed by shaking the solution.

The result shows that GMP alone does not provide stable suspension of dispersed SWNTs. Analogous experiments could not be performed for Guo since it is insoluble in water.

Binary G-gel 1

Second, SWNTs were solubilized in a binary G-gel (Gel 1) comprised of 20 mM Guo, 250 mM GMP, (GUO:GMP ratio of 1:12.5) 50 mM KCl in 25 mM Tris buffer, pH 7.2.

Suspensions of 5 µg/mL, 10 µg/mL, 20 µg/mL, 50 µg/mL, 100 µg/mL and 2 mg/mL SWNT in Gel 1 were evaluated for solubilization, dispersion and viscosity. These suspensions were liquid between 2-25° C. at SWNT concentrations<1 mg/mL. At higher SWNT concentration, the suspensions exhibit thermoassociative behavior, forming gels at room temperature. Suspensions of as much as 5 mg/mL SWNT were stable, showing no signs of degradation or precipitation after 4 weeks.

When inverted, a vial containing 50 ug/mL SWNT in Gel 1 flowed to the bottom (inverted top) of the vial. However, a solution of 2 mg/mL SWNT in Gel 1 remained in the top (inverted bottom) of the vial as a gel when inverted.

Binary G-gel 2

Third, SWNTs were solubilized in a binary G-gel (Gel 2) comprised of 60 mM Guo, 300 mM GMP, (GUO:GMP ratio of 1:5) 50 mM KCl in the same buffer as Gel 1. Gel 2 was found to be thermoassociative even in the absence of SWNT, forming gels at temperatures≧33° C.

Suspensions of 6 µg/mL, 12 µg/mL, 30 µg/mL, 60 µg/mL, 120 µg/mL and 240 µg/mL SWNT in Gel 2 were evaluated for solubilization, dispersion and viscosity.

The gelation temperature was found to decrease with increasing SWNT concentration until, above 2 mg/mL SWNT, the suspension is a gel even at 2° C. Concentrations as high as 2.4 mg/mL could be suspended in G-gel 2.

For both Gels 1 and 2, recovery of SWNTs could be achieved by heating the suspension above its melting temperature, causing the SWNTs to precipitate.

Example 7

Optical Microscopy

Optical microscopy using a simple light microscope at a resolution of 200×, was performed on G-gels with and without SWNTs. Gels were prepared with 10 ug/mL SWNT or no SWNT and allowed to dry. In both cases the dehydrated gel exhibited crystallinity but the crystallinity was more pronounced and regular in the presence of SWNTs. These results suggest that SWNTs promote the self-assembly of the gels and become an integral part of the gel structure.

Example 8

Scanning Electron Microscopy (SEM) and Atomic Force Microscopy (AFM) of SWNT

Atomic force microscopy (AFM) of 2 mg/mL SWNT in Gel 1 showed well-dispersed SWNTs with diameters of ~2 nm (from line scan analysis), which is consistent with diameters of ~0.9-1.7 nm that were obtained from micro-Raman spectra of the radial breathing mode (see Example 9 below).

The average length of the suspended SWNTs is 1 µm, which is similar to their length in the starting material. Thicker regions of the SWNTs were observed and may be individual or bundled SWNTs, or G-gel bridges between adjacent SWNTs.

Atomic force microscopy (AFM) of 240 µg/mL SWNT in Gel 2 showed that SWNTs were individually dispersed in the gel. There was evidence of parallel alignment suggesting a high degree of organization that might be increased by optimization of experimental conditions and application of an electric field. The presence of a thicker structures observed in the image may be evidence of different modes of interaction between the gel and the various structures in the heterogeneous SWNT preparation, or to solubilization of both bundled and monodispersed nanotubes.

Example 9

Raman Spectroscopy of SWNTs

Micro-Raman spectroscopy was performed of the Radial Breathing Mode (RBM) region (100-300 $cm^{-1}$) and the G-Band region (1400-1700 $cm^{-1}$) for acid treated SWNTs in aqueous suspension (reference sample) and for 1 mg/mL SWNTs in Gel 1 after one week and from the top and bottom of the gel after four weeks. Relative intensity was measured against Raman shift ($cm^{-1}$).

Calculations of others have shown that SWNTs with diameters d<1.1 nm are metallic with RBM frequencies of 218-280 $cm^{-1}$, while SWNTs with d>1.1 nm are semiconducting with RBM frequencies of 175-213 $cm^{-1}$. (Rao, A. M., et al., Phys. Rev. Lett., 2001, 86, 3895).

Here, it was found that the peaks in both regions are blue-shifted by 5-7 $cm^{-1}$ in the G-gel relative to the reference, which is evidence of interactions between the SWNTs and the G-gel structures (Dresselhaus, M. S. et al., Carbon 2002, 40, 2043). Compared to the reference, the peaks associated with the semiconducting SWNTs in the G-gel samples were diminished, indicating that the metallic tubes are preferentially solubilized in the G-gels relative to the semiconducting tubes (Krupke, R., et al., Am. Chem. Soc. 2003, 125, 3370).

Furthermore, the spectra of the suspensions after 4 weeks show evidence of selective enrichment from top to bottom of different structures within each class of SWNTs. Most notable were the relative increases of the semiconductor peak at 186 $cm^{-1}$ and the metallic peak shoulder at 272 $cm^{-1}$ in the top of the gel and the increase of the semiconductor peak at 206 $cm^{-1}$ in the bottom of the gel.

In the G-band region (1400-1700 $cm^{-1}$), the sharp peak of the semiconducting SWNTs was blue shifted from 1587 $cm^{-1}$ in the reference to 1592 $cm^{-1}$ in the G-gel suspension, which is evidence of association with the G-gel matrix. The shoulder near 1565 $cm^{-1}$, also attributed to semiconducting nanotubes, was less distinct in the gel and indiscernible in the sample taken from the top of the 4-week suspension.

In contrast, the broad peak of the metallic SWNTs (Dresselhaus, M. S.; et al., Carbon 2002, 40, 2043; Krupke, R. et al., Science 2003, 301, 344; and Chattopadhyay, D., et al., J. Am. Chem. Soc. 2003, 125, 3370) at 1540 $cm^{-1}$ was much more prominent in the G-gel than reference, especially in the sample taken from the top of the gel after 4 weeks.

These results indicate that G-gels solubilize high concentrations of SWNTs with preferential dispersion and enrichment of metallic tubes, and suggest that, as the sample ages, the SWNTs within the two classes are further distributed based on their chirality.

Example 10

Circular Dichroism Spectroscopy of SWNTs

The circular dichroism spectrum of 5 mg/mL SWNT in gel showed increased magnitudes of the positive peak at 220 nm and a negative peak at 260 nm relative to the spectrum of the gel in the absence of SWNTs. It is known that 220 nm indicates the formation of G quartet and 260 nm signals formation of secondary structure. The addition of SWNT in high concentration to the thermoassociative gels was found to destroy their thermoassociative (TA) property.

The CD results suggest that addition of carbon nanotubes results in an increase in the concentration of G-quartet in solution while concomitantly destroying or changing second structures. Based upon this finding, it is possible that the pi-pi interaction between G-quartet and SWNT may be the driving force for dispersion.

While this invention has been particularly shown and described with references to preferred embodiments thereof, it will be understood by those skilled in the art that various changes in form and details may be made therein without departing from the scope of the invention encompassed by the appended claims.

What is claimed is:

1. A binary guanosine gel comprising guanosine (GUO) and guanosine 5' monophosphate (GMP) wherein the ratio of GUO:GMP is from about 0.08 to about 0.25.

2. The binary guanosine gel of claim 1 wherein the ratio of GUO:GMP is 0.25.

3. The binary guanosine gel of claim 1 wherein the ratio of GUO:GMP is 0.2.

4. The binary guanosine gel of claim 1 wherein the ratio of GUO:GMP is 0.08.

5. The binary guanosine gel of claim 1 having a viscosity which is higher at room temperature than its viscosity at a temperature less than room temperature.

6. The binary guanosine gel of claim 1 having a pH in the range of between about 5 and about 9.

7. The binary guanosine gel of claim 1 having a potassium chloride concentration of at least 0.01 M.

8. A method of enriching the fraction of metallic nanotubes in a sample comprising solubilizing individual single walled carbon nanotubes (SWNTs) in the binary guanosine gel of claim 1 or 3.

9. A method of partitioning single walled carbon nanotubes (SWNTs) by chirality comprising solubilizing said SWNTs in the binary guanosine gel of claim 1 or 3.

10. The binary guanosine gel of claim 1 or 3 further comprising a carbon nanotube.

11. The binary guanosine gel of claim 10, wherein the carbon nanotube is a single walled carbon nanotube (SWNT).

12. The binary guanosine gel of claim 1 further comprising a living cell.

13. The binary guanosine gel of claim 1 further comprising an enzyme.

14. The binary guanosine gel of claim 1 further comprising a drug.

* * * * *